(12) United States Patent
Aszmann et al.

(10) Patent No.: US 11,607,544 B2
(45) Date of Patent: Mar. 21, 2023

(54) DEVICE AND METHOD FOR INFLUENCING A PATIENT'S GAIT

(71) Applicant: NSTIM SERVICES GMBH, Vienna (AT)

(72) Inventors: Oskar Aszmann, Vienna (AT); Hans Dietl, Gablitz (AT); Andreas Goppelt, Vienna (AT); Christian Hofer, Vienna (AT); Michael Friedrich Russold, Vienna (AT); Ernesto Urbano, Vienna (AT)

(73) Assignee: NSTIM SERVICES GMBH, Vienna (AT)

( * ) Notice: Subject to any disclaimer, the term of this patent is extended or adjusted under 35 U.S.C. 154(b) by 0 days.

(21) Appl. No.: 16/317,516

(22) PCT Filed: Jul. 26, 2017

(86) PCT No.: PCT/EP2017/068903
§ 371 (c)(1),
(2) Date: Jan. 11, 2019

(87) PCT Pub. No.: WO2018/019893
PCT Pub. Date: Feb. 1, 2018

(65) Prior Publication Data
US 2019/0224479 A1    Jul. 25, 2019

(30) Foreign Application Priority Data
Jul. 29, 2016  (EP) .................................. 16181996

(51) Int. Cl.
*A61N 1/36* (2006.01)
*A61B 5/11* (2006.01)
(Continued)

(52) U.S. Cl.
CPC .......... *A61N 1/36003* (2013.01); *A61B 5/112* (2013.01); *A61B 5/4836* (2013.01);
(Continued)

(58) Field of Classification Search
CPC .. A61N 1/36003; A61N 1/0452; A61B 5/112; A61B 5/4836
See application file for complete search history.

(56) References Cited

U.S. PATENT DOCUMENTS

| 5,121,747 A * | 6/1992 | Andrews ............ A61N 1/36003 602/16 |
| 7,403,821 B2 | 7/2008 | Haugland et al. |

(Continued)

FOREIGN PATENT DOCUMENTS

| CN | 101801456 A | 8/2010 |
| CN | 102580240 A | 7/2012 |

(Continued)

OTHER PUBLICATIONS

PCT International Search Report for PCT International Patent Application No. PCT/EP2017/068903, dated Nov. 15, 2017.
(Continued)

*Primary Examiner* — Allen Porter
*Assistant Examiner* — Adreanne A. Arnold
(74) *Attorney, Agent, or Firm* — Holland & Hart LLP

(57) ABSTRACT

A device for influencing a patient's gait, comprising at least one foot lifter stimulation electrode for activating a foot lifter muscle, at least one sensor unit, at least one hip flexor stimulation electrode for activating a hip flexor muscle, and at least one control unit which is coupled to the sensor unit and the stimulation electrodes, processes sensor values from the sensor unit and, depending on the sensor values, activates at least one of the stimulation electrodes.

18 Claims, 4 Drawing Sheets

(51) Int. Cl.
    *A61B 5/00*     (2006.01)
    *A61N 1/05*     (2006.01)
    *A61N 1/04*     (2006.01)

(52) U.S. Cl.
    CPC ......... *A61N 1/0452* (2013.01); *A61N 1/0556* (2013.01); *A61B 2562/0219* (2013.01)

(56) References Cited

U.S. PATENT DOCUMENTS

| | | | |
|---|---|---|---|
| 8,452,410 B2 | 5/2013 | Emborg et al. | |
| 2003/0014087 A1* | 1/2003 | Fang | A61N 1/025 607/48 |
| 2003/0093021 A1 | 5/2003 | Goffer | |
| 2009/0024065 A1 | 1/2009 | Einarsson | |
| 2012/0059432 A1* | 3/2012 | Emborg | A61N 1/36003 607/49 |
| 2012/0197343 A1* | 8/2012 | Lane | A61B 5/6829 607/49 |
| 2012/0226330 A1 | 9/2012 | Kolen et al. | |
| 2012/0330395 A1* | 12/2012 | Dar | A61B 5/1038 607/149 |
| 2013/0338734 A1 | 12/2013 | Hoyer et al. | |
| 2014/0058476 A1 | 2/2014 | Crosby et al. | |
| 2014/0094345 A1 | 4/2014 | Kim et al. | |
| 2015/0100105 A1 | 4/2015 | Kiani et al. | |
| 2017/0202724 A1* | 7/2017 | De Rossi | A61F 5/01 |
| 2018/0318583 A1* | 11/2018 | Mcbride | A61B 5/112 |

FOREIGN PATENT DOCUMENTS

| | | |
|---|---|---|
| CN | 102596311 A | 7/2012 |
| CN | 105263569 A | 1/2016 |
| CN | 105992554 A | 10/2016 |
| EP | 1257318 B1 | 12/2006 |
| WO | 2009/014644 A1 | 1/2009 |

OTHER PUBLICATIONS

Chinese Patent Office, "Office Action," issued in connection with Chinese Patent Application No. 201780046396.5 dated Sep. 2, 2022 (12 pages) (Original Document only).

\* cited by examiner

DEVICE AND METHOD FOR INFLUENCING A PATIENT'S GAIT

TECHNICAL FIELD

The invention relates to a device and method for influencing a patient's gait, comprising at least one foot lifter stimulation electrode for activating a foot lifter muscle and at least one control unit which is coupled to a sensor unit, processes sensor values from the sensor unit and, depending on the sensor values, activates a stimulation electrode. The invention likewise relates to a method for influencing a patient's gait using such a device.

BACKGROUND

U.S. Pat. No. 7,403,821 B2 discloses a method for generating a dorsiflexion of a patient's foot, in which stimulation electrodes and signal capture electrodes are arranged on at least one peripheral nerve of the thigh. Neural signals are recorded and processed via the electrodes in order to determine a movement or an action which indicates the time of a heel strike or a heel lift during walking. Depending on the detected action, the stimulation electrode is activated in order to generate a dorsiflexion of the foot of the patient.

EP 1 257 318 B1 relates to a device for generating a dorsiflexion and for stimulating motor nerve fibres, comprising means for receiving and processing the detected nerve signals and for generating stimulation signals, wherein the device comprises a combined detection and stimulation electrode device and is designed as a combined electrode. Means are envisaged for switching each combined electrode between a detection state and a stimulation state. The combined detection and stimulation electrode device is designed to be implantable.

Furthermore, it is known from the prior art, in the case of drop foot, to arrange surface electrodes as stimulation electrodes on the skin in the region of the lower leg in order to control a stimulation signal via a heel switch. If the heel is stressed during walking or standing, the stimulation electrodes are not activated, and so a patient can roll over the foot during walking without tension of the foot lifter musculature. Once the heel is relieved, the switch is operated and a stimulation signal is given to the electrode, and so a muscle activation in relation to dorsiflexion can take place. Such a device is provided by OttoBock Healthcare under the name "MyGait".

The activation of nerves in relation to muscle stimulation serves to facilitate walking for patients suffering from a peroneus weakness. Patients suffering from a peroneus weakness have the problem that the tip of the foot falls downwards during lifting of the foot ("drop foot"). The result of this is that the foot has to be lifted abnormally to avoid a dragging of the tip of the foot during swing-through, resulting in an impairment of the gait.

Frequently, the problem for drop foot patients is that the peroneal nerve was not damaged in isolation, but that the cause of the damage to the peroneal nerve also impairs the rest of the gait.

It is an object of the present invention to provide a device and a method which can further improve the gait of a patient.

SUMMARY

According to the invention, this object is achieved by a device having the features of the present invention and a method having the features of the present invention. Advantageous designs and developments of the invention are disclosed in the description and the figures.

The device for influencing a patient's gait, comprising at least one foot lifter stimulation electrode for activating a foot lifter muscle and at least one sensor unit, envisages that at least one hip flexor stimulation electrode for activating a hip flexor muscle is provided, with at least one control unit being coupled to the at least one sensor unit and the stimulation electrodes, with the control unit processing sensor values transmitted from the sensor unit to the control unit and, depending on the sensor values, at least one stimulation electrode being activated. What is thus made possible by the device according to the invention is that not only can the gait be improved via a time-controlled or load-controlled activation of a foot lifter muscle, but that, as a result of a specific activation of the hip flexor musculature, hip flexion is activatable or supported in order to thus activate additional energy for walking. To activate the hip flexor musculature, the muscle in question can be activated either directly or via a nerve used as signal conductor, and so an additional energy is introduced into the system via the electrically activated musculature. In addition to the hip flexion, the foot lifter stimulation electrode is activated and deactivated in temporal or load-dependent coordination with the hip flexor stimulation, and so a signal is transmitted to the foot lifter stimulation electrode during lifting of the foot, for example during toe-off, during walking. This allows a slight swing-through of the foot without the need for a circumduction of the leg.

The foot lifter stimulation electrode can be designed as a surface electrode because the profile of the main activation nerve is relatively close to the surface. As an alternative to a surface electrode, the foot lifter stimulation electrode(s) can be designed as an implant or implants which are preferably placed around the particular nerve as a cuff or as electrode plates. Via the implants, it is possible to achieve a permanent and reliable assignment of the electrodes to the particular nerve. What is required here is a one-off implantation of the stimulation electrode, which can be in the form of either a full implant or an implant having a percutaneous portion, in order to allow a wire-based pulse from the control unit through the skin to the electrode. The electrode line leads from the stimulation site on the nerve through the skin to an external pulse generator, the so-called stimulator, which is activated by the control unit by an appropriate signal being applied thereto. Percutaneous stimulation electrodes are preferably positioned in the immediate vicinity of the nerve branches innervating those muscles responsible for the particular muscle contraction and flexion. Such a percutaneous stimulation electrode can also be used for the hip flexor stimulation, the hip flexor stimulation electrode preferably being designed as an implant, since the hip flexor musculature can be activated only with difficulty via a surface electrode.

Independent of whether they cause a dorsiflexion of the foot or a hip flexion, implanted electrodes, can, besides the design as percutaneous stimulation electrodes, also be designed as a hybrid implant, in which a cable leads from the electrode to an implanted pulse generator, which is likewise implanted and is preferably placed beneath and in the vicinity of the skin surface. In this case, there is no skin penetration. Supply of energy to and control of the particular electrode is achieved via a sending and receiving unit placed directly on the skin surface above the pulse generator, and so a transfer of energy and information to the electrode can be effected. Inversely, a back-transfer of information from the electrode to the sending and receiving unit is effected in order to obtain a feedback via the exercised pulse. The transport of information thus takes place bidirectionally, and the transfer of energy takes place only unidirectionally.

Besides a hybrid implant, the electrode can also be designed as a full implant, in which not only the electrode but also the pulse generator, the energy supply and the control unit are designed as an implant. The supply of energy takes place either via a battery or a rechargeable battery. A wireless connection from the implant to the outside, i.e. outside the patient's body, is envisaged in order to perform adjustments or to be able to read data.

Independent of whether it is designed as a hip flexor stimulation electrode or foot lifter stimulation electrode, each stimulation electrode can be coupled to a common control unit. As an alternative to a common supply to the electrodes of particular signals and possibly energy, it is possible for the at least one foot lifter stimulation electrode to be coupled to a first control unit and the at least one hip flexor stimulation electrode to be coupled to a separate, second control unit, for example in order to be able to construct the device in a modular manner or in order to be able to more easily carry out adjustments of the control program to the muscle group required in each case.

One development of the invention envisages that the control unit is constructed in a hierarchical manner, with the foot lifter stimulation being designed as the leading system. The foot lifter stimulation as the leading system has the advantage that the initially important function, namely the avoidance of a stumbling or dragging of the foot with the tip of the foot during swing-through, is prioritized and the hip flexor stimulation is carried out depending on the triggering of a dorsiflexion, and so an improved gait can be achieved even without hip flexor stimulation.

The implanted stimulation electrodes can be inductively coupled to an external signal processing unit via an implanted receiving unit in order to receive necessary signals, for example from sensors, or to allow changes in the control sequences for adaptation to a patient or a changing gait.

It is likewise possible for an implanted control unit to be provided with an inductively rechargeable, implantable energy store and/or a signal processing unit in order to provide a full implant which can function autonomously. In this case, the implanted control unit is coupled to the rechargeable, implantable energy store. Rechargeability increases the service life of the device during operation. The signal processing unit allows the processing of sensor signals, especially of implanted sensor signals, with the stimulation electrode being able at the same time to be also designed as a sensor in order to capture data concerning forces, momenta, accelerations and/or positions of the particular extremity in which the sensor is implanted. Preferably, the sensors are arranged distally as far as possible, i.e. as distally as possible in relation to the knee joint in the case of the present device, since the quality of the signals over the walk profile is better the closer the sensor is arranged relative to the ground.

The sensor unit can comprise an acceleration sensor or acceleration sensors, a position sensor or position sensors, a momentum sensor or momentum sensors and/or a force sensor or force sensors, which are assigned to the particular control unit in order to obtain therethrough the necessary information with respect to the walk behaviour of the patient. Especially in the case of a full implant comprising a control system and sensor system, a thigh-side arrangement of the sensors, especially of the acceleration sensors and the position sensors, is envisaged and advantageous.

The control system and the sensors can be implanted collectively as a common module.

Besides an implanted sensor unit or an implantably designed sensor unit, it is possible for the sensor unit to be fixed on an orthotic component or form said component. For example, the sensor can be designed as a switch and be arranged on a shoe, a buckle, an ankle brace or a similar orthotic device. The sensor unit can also be fixed on the leg of the patient, for example in the region of the foot, the heel, the ankle or the lower leg, directly on the leg, for example it can be adhesively bonded or be immobilized thereon via a fastening element such as a belt, strap or elastic bandage or cuff.

The control unit too can be designed to be implantable. The arrangement of all sensor units distally to the knee joint improves the accuracy of the sensor signals.

An inductive energy and information transfer unit can be assigned to the control unit in order to be able to wirelessly transfer signals and energy to the control unit.

The method for influencing the gait of a patient using a device as described above envisages that forces acting on the foot, the thigh and/or the lower leg of the patient, the correspondingly occupied positions, the accelerations of the foot, of the thigh and/or of the lower leg and/or momenta acting on the foot, the thigh and/or the lower leg are captured via the sensor unit and that the sensor values captured by the at least one sensor unit are transmitted to the control unit. Via the at least one foot lifter stimulation electrode, at least one foot lifter muscle of the patient is activated, with the at least one hip flexor stimulation electrode being activated depending on the activation of the foot lifter muscle, and so, for example, the foot lifter stimulation is triggered after the heel-off or after the toe-off in order to prevent the forefoot from dragging on the ground during the swing phase. If the foot lifter muscle is activated or if multiple foot lifter muscles are activated, a hip flexor muscle is activated via the hip flexor stimulation electrode at the same time or at a chronological interval therefrom in order to bring about a contraction of the hip flexor muscle and to thereby influence the walk behaviour of the patient.

The stimulation electrodes can be activated via a common control unit, and so sensor data concerning the state of the foot, the position of the foot or of the lower leg, the acting forces or similar influencing variables on the foot and/or lower leg or thigh converge in a common control unit and the activation of both muscles or muscle groups is induced or interrupted via said common control unit. Via the sensor signals, a feedback also takes place as to whether and to what extent the activation of the particular muscle was successful, and so, for example, it is possible to determine via position sensors whether and to what extent a raising of the tip of the foot was achieved or whether and to what extent a lower leg was swiveled. Via said sensor signals, there is then a feedback to the control unit and possibly an adjustment of the intensity of the stimulation signals.

The stimulation electrodes can be activated wirelessly by the particular control unit, and so there is no need for skin penetration in order to send control signals to the stimulation electrodes. One possibility therefor is provided by implantable or implanted myoelectric sensors.

One variant of the invention envisages that a first stimulation electrode is activated by a first control unit and a second stimulation electrode is activated by a second control unit, with both control units being able to communicate with one another wirelessly in order to coordinate the particular activation of the muscle or of the muscle groups.

BRIEF DESCRIPTION OF THE DRAWINGS

Hereinbelow, exemplary embodiments of the inventions will be more particularly elucidated with reference to the accompanying figures, where:

FIG. 1 shows a first variant of the invention, in which a first control unit 31 is designed to be externally fixable on a patient. The first control unit 31 is connected via wires to two surface stimulation electrodes 11 which are to be arranged and are arranged on the patient such that they can stimulate a foot lifter muscle. The primary stimulation of the foot-lifting musculature is effected via the deep peroneal nerve, which runs beneath the skin close to the surface in the region of the knee joint and can be stimulated via one via multiple surface electrodes 11.

DETAILED DESCRIPTION

Figure 1:
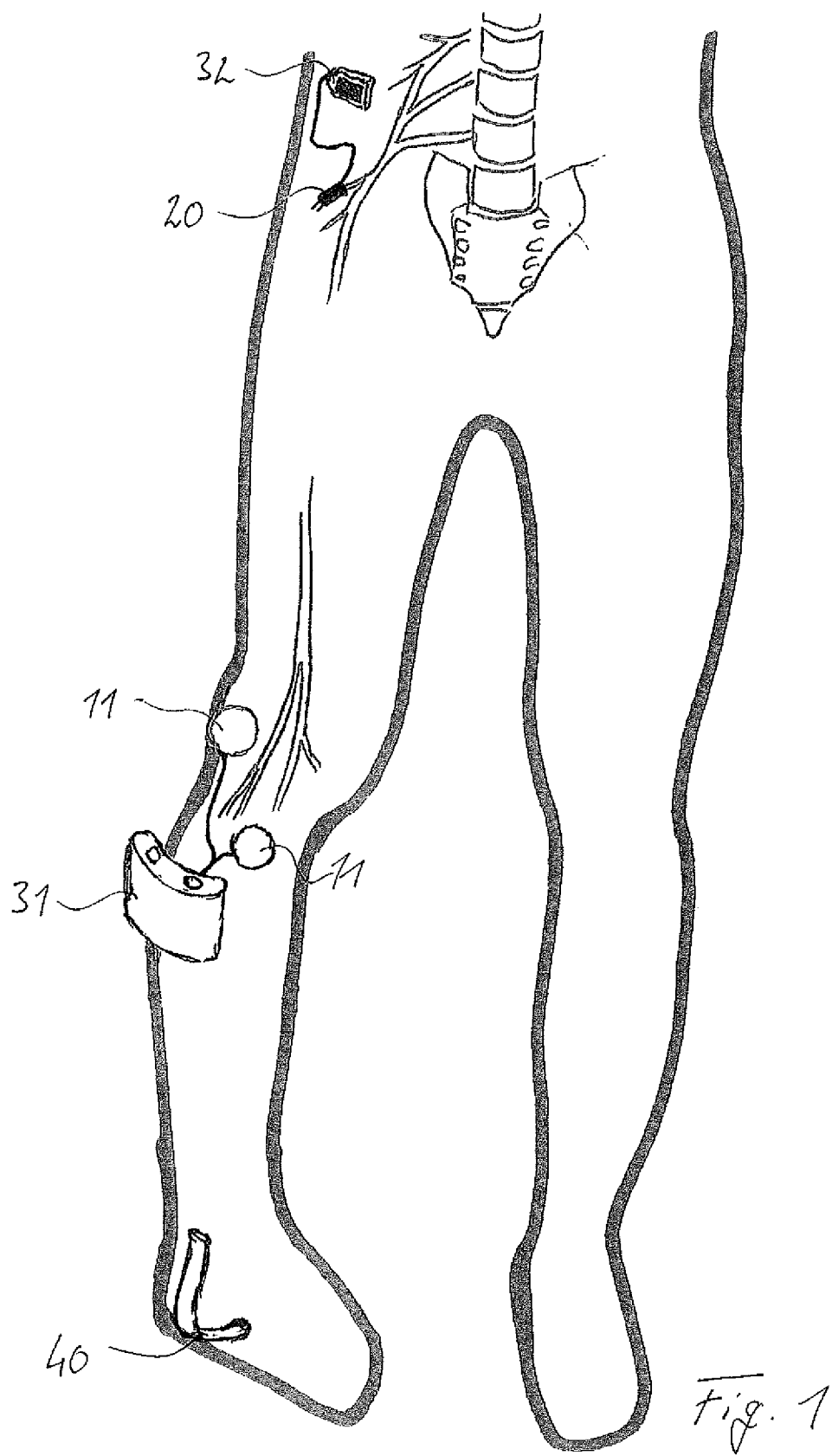
FIG. 1—shows a schematic representation of a device comprising an external sensor, a surface stimulation electrode and an implanted hip flexor stimulation electrode.

In the hip region, a second electrode is implanted as a hip flexor stimulation electrode 20. The hip flexor stimulation electrode 20 is designed as a cuff or so-called cuff electrode and coupled to a likewise implanted second control unit 32. The hip flexor stimulation electrode 20 is coupled to the second control unit 32 in the depicted exemplary embodiment by means of a wire; in principal, it is also possible to design a wireless coupling, for example via implantable or implanted myoelectric sensors.

Furthermore, a sensor unit 40 is arranged on the foot exterior and below the sole of the foot. The sensor unit 40 is designed as a strap and can be fixed directly on the foot. Alternatively, such a sensor unit can be arranged in a shoe or in an orthotic device, for example an orthosis, a bandage or a cuff, and thus be permanently assigned to the foot or the lower leg. The sensor unit 40 can comprise multiple sensors which represent different parameters. For instance, it is possible to capture pressure forces, momenta, accelerations or positions. To this end, the sensors can be designed as switches, pressure sensors, position sensors, strain gauges, gyroscopes, momentum sensors, acceleration sensors or the like. The sensor unit 40 is coupled wirelessly to the control units 31, 32 and transmits the respective sensor values to the control units 31, 32 if said values are relevant for the particular control unit 31, 32.

In the depicted exemplary embodiment, the relationship between the first control unit 31 for controlling the foot lifter stimulation and the second control unit 32 for controlling the hip flexor stimulation is constructed in a hierarchical manner. This means that sensor values determined via the sensor unit 40 are transmitted either only to the first control unit 31 or to both control units 31, 32 and an evaluation takes place in the first control unit 31. If the evalution leads to an outcome of a foot lifter stimulation needing to be carried out, the foot lifter stimulation electrode(s) 11 is/are activated. At the same time, the control unit 32 can transmit an appropriate stimulation signal for the hip flexor muscle to the hip flexor stimulation electrode 20. It is likewise possible to envisage an appropriate time control based on empirical values, and so a hip flexor stimulation takes place only with a predetermined temporal delay after the foot lifter stimulation. It is also possible for the first control unit 31, after activation of the foot lifter stimulation electrodes 11, to send a stimulation signal to the second control unit 32, which then forwards the appropriate stimulation pulse, possibly after an appropriate amplification of the signal, in order to thereby activate the hip flexor musculature.

Figure 2:
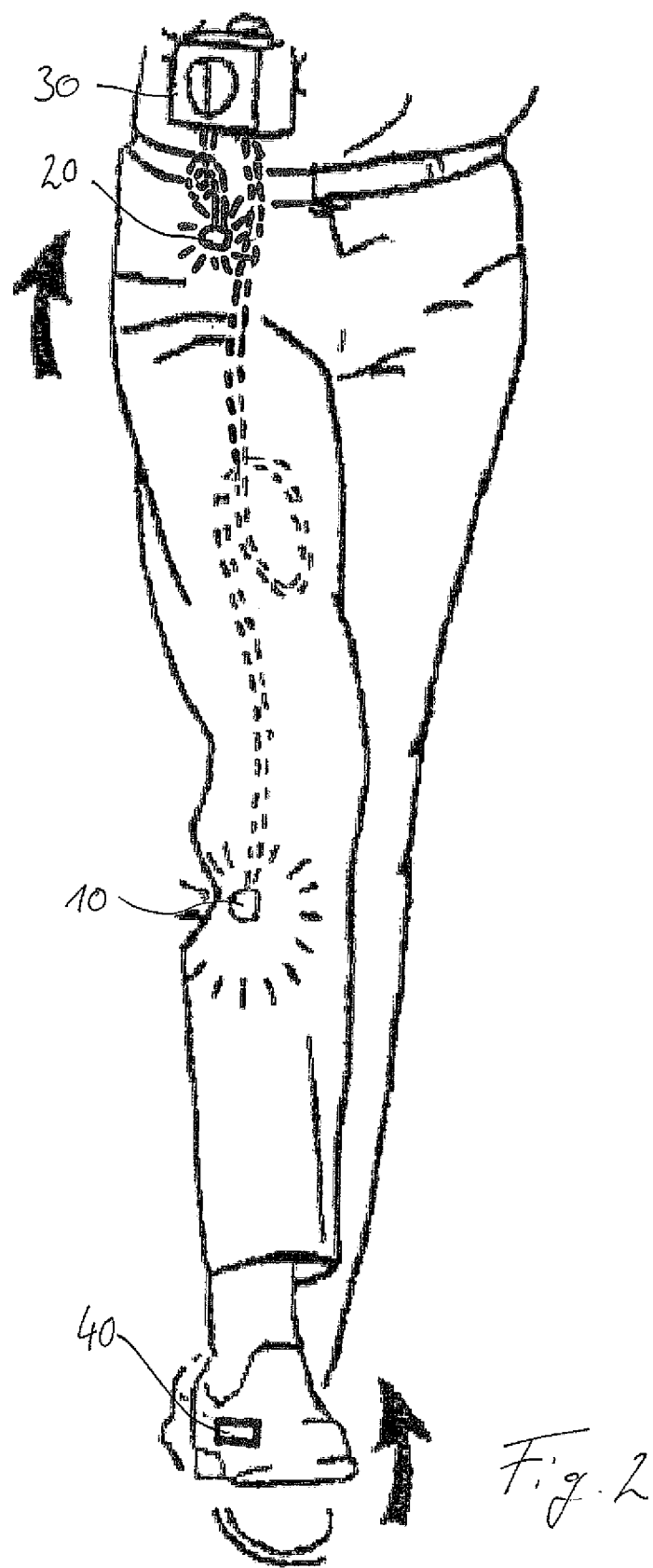
FIG. 2—shows one variant of the invention comprising a common control unit.

One variant of the invention is depicted in FIG. 2, in which a common control unit 30 is coupled wirelessly to the sensor unit 40. In the depicted exemplary embodiment, the sensor unit 40 is integrated in a shoe; other fixing means or arrangements on or in a foot can be envisaged. In the depicted exemplary embodiment, both electrodes 10, 20 are designed as implants and surround an appropriate nerve at least in part. Furthermore, the electrodes 10, 20 can be designed to pick up signals in order to exercise not only a pure stimulation function but also a detection function, so as to be able to detect nerve signals. In the depicted exemplary embodiment, the electrodes 10, 20 are designed as so-called hybrid implants, in which a cable leads from the electrode to an implanted pulse generator or signal generator. The pulse generator or signal generator is placed beneath the skin surface and can likewise be designed to be magnetic. Without any skin penetration, a supply of energy and a transfer of signals then takes place directly on the skin surface through the skin, for example inductively, in order to control the particular electrode 10, 20. It is also possible for the electrodes to be designed as percutaneous electrodes, in which a coupling site on the skin surface with a penetration of the skin is provided via a conductor. The conductor can be designed as a contact surface, for example a contact surface designed to be magnetic, to which a corresponding contact surface of a conductor coupled to the common control unit 30 can then be coupled.

In the region of the electrodes 10, 20, it is also possible to arrange or integrate sensors which bring about an exchange of information with the control unit 30 via the pulse generator or the contact surface. Electrodes and sensors can be designed in collective form to give a modular unit.

Figure 3:
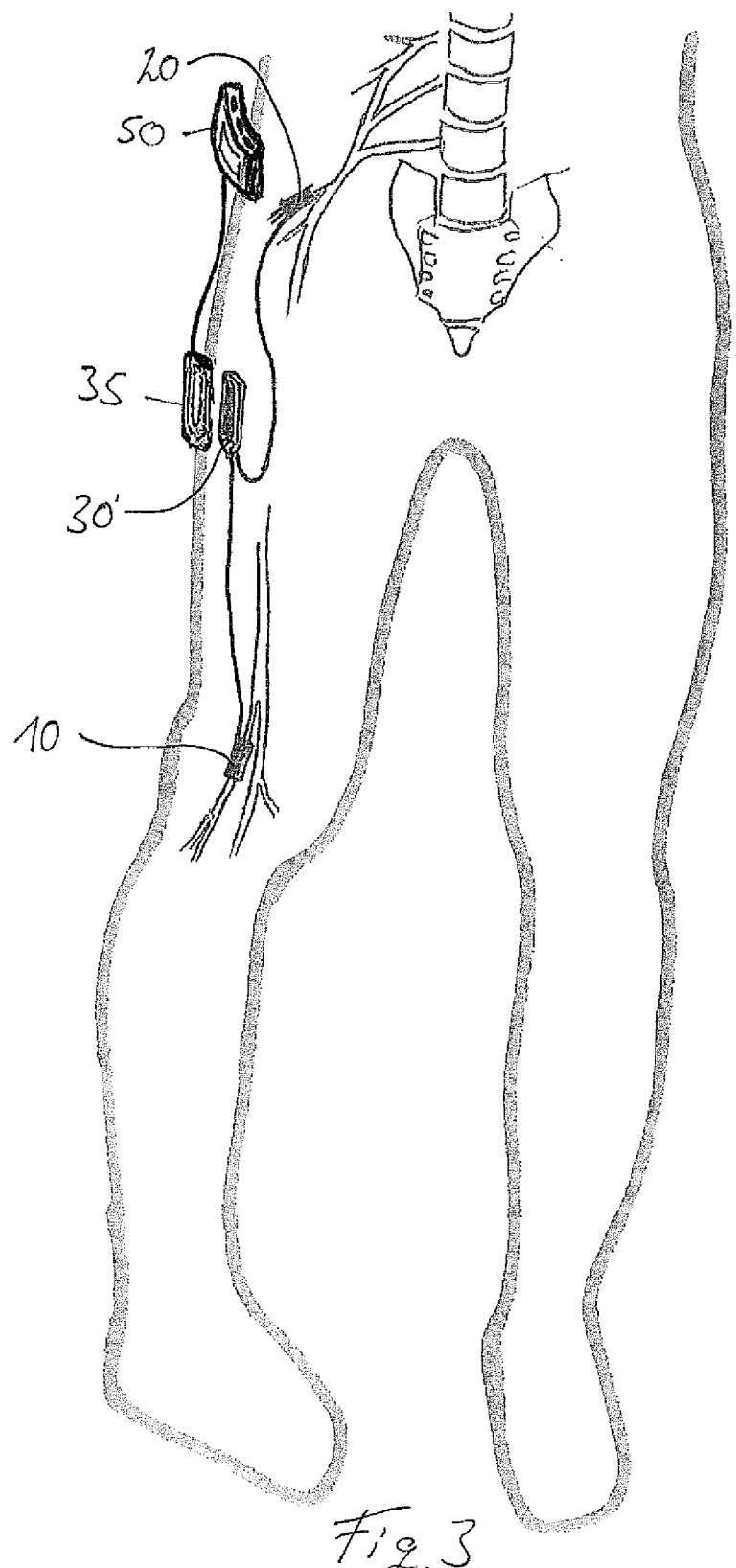
FIG. 3—shows one variant of FIG. 2 comprising a control unit with a wireless means of energy and signal transfer.

One variant of the invention is shown in FIG. 3, in which again two implanted electrodes 10, 20 are arranged in the region of the hip flexor musculature and the foot lifter musculature on the respective innervating nerves. The implanted electrodes 10, 20 are jointly connected to a receiving unit 30', which is likewise implanted. The receiving unit 30' is arranged in the region of the skin surface and serves as a signal receiver and as an energy receiver and possibly also as an energy store. On the exterior of the receiving unit 30', there is arranged on the skin exterior an energy and information transfer unit 35, which, for example, is clearly assignable to the receiving unit 30' by magnetic means. This ensures an adhesion of the energy and information transfer unit 35 to the receiving unit 30', without a disengagement of the energy and information transfer unit 35 posing difficulties. The energy and information transfer unit 35 is coupled by cable to a control unit 50, which, on the basis of the sensor data provided by the no longer depicted sensor unit, causes the stimulation of the particular muscles or muscle groups. The computing power for the processing of the sensor signals and for generating a load-controlled and/or time-controlled stimulation signal is situated in the control unit 50, and so the electrodes 10, 20 as well as the receiving unit 30' can be designed to be small and minimally burdening in order to facilitate an implantation.

Figure 4:
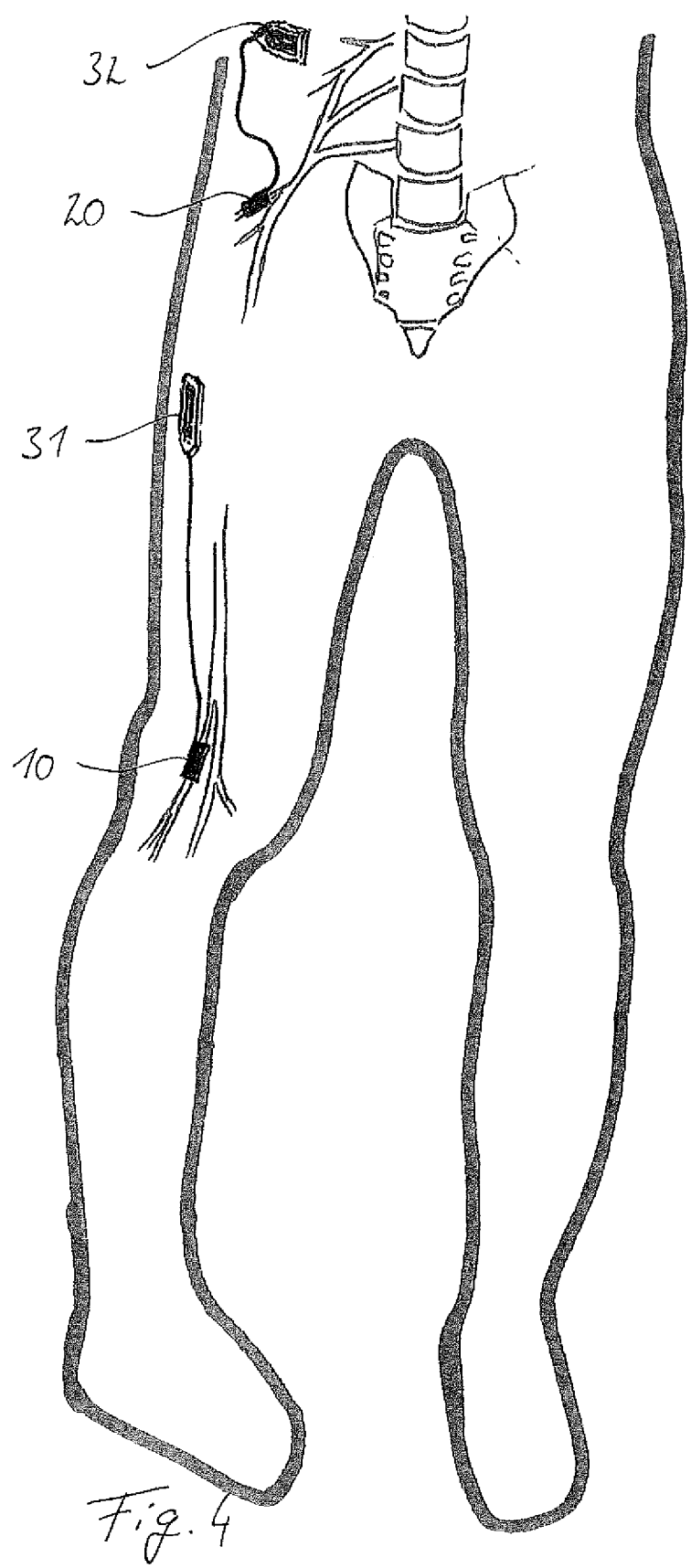
FIG. 4—shows one variant of the invention comprising separate control units.

A further variant of the invention is depicted in FIG. 4, in which two separate control units 31, 32 are designed to be implantable and implanted. Both control units 31, 32 are coupled to separate, likewise implanted electrodes 10, 20, and so each control unit 31, 32 is responsible for the activation of a muscle or a muscle group. The separate control units 31, 32 are coupled to one another wirelessly in order to be able to ensure a communication and thus a temporally coordinated pulse or a pulse sequence for activating the particular musculature. If, at first, the foot lifter muscle is activated by the first control unit 31 and the foot lifter stimulation electrode 10, so that the corresponding foot lifter muscle contracts, this is, optionally after a response by means of a detection unit within the electrode 10, transmitted to the second control unit 32, which, immediately thereafter or with a temporal delay, causes an activation of the hip flexor musculature by stimulating the corresponding nerve with the hip flexor stimulation electrode 20. The two separate control units 31, 32 can be provided with an energy store in the form of a battery or a rechargeable battery. A supply of energy can be effected with induction. An additional transfer of data can be effected wirelessly, making possible a connection of the particular implant to an external unit. The purpose of said connection is to be able to perform adjustments within the control system and to read data.

The stimulation of the musculature can be performed via one or more channels. This means that multiple muscles or muscle groups which are required for hip flexion and/or dorsiflexion of the foot can too be activated in order to harmonize movement and to improve gait. In particular, the resulting movement in the hip can be controlled better, for example by performing or preventing an external rotation of the thigh.

The invention claimed is:

1. A device for influencing a patient's gait, comprising;
    at least one foot lifter stimulation electrode for activating a foot lifter muscle;
    at least one sensor unit;
    at least one implanted implantable hip flexor stimulation electrode for activating a hip flexor muscle;
    at least one control unit, which is coupled to the sensor unit and the foot lifter and hip flexor stimulation electrodes, processes sensor values from the sensor unit and, depending on the sensor values, activates at least one of the foot lifter and hip flexor stimulation electrodes, the at least one control unit being constructed in a hierarchical manner to actuate the at least one foot lifter stimulation electrode followed by actuating the at least one implantable hip flexor stimulation electrode.

2. The device according to claim 1, wherein the at least one foot lifter stimulation electrode is designed as a surface electrode or as an implant, and the hip flexor stimulation electrode is designed as an implant.

3. The device according to claim 1, wherein each stimulation electrode is coupled to a common control unit or the at least one foot lifter stimulation electrode, and the at least one hip flexor stimulation electrode is coupled to a separate control unit.

4. The device according to claim 1, wherein the stimulation electrodes are inductively coupled to an external signal processing unit via an implanted receiving unit.

5. The device according to claim 1, wherein an implanted control unit is provided with at least one of an inductively rechargeable, implantable energy store and a signal processing unit.

6. The device according to claim 1, wherein the sensor unit is designed for at least one of capturing at least one of forces, momenta and accelerations exercised on a lower extremity of the patient and capturing positions of the lower extremity.

7. The device according to claim 1, wherein the sensor unit comprises at least one of acceleration sensors, position sensors and force sensors, which are assigned to the control unit.

8. The device according to claim 1, wherein the sensor unit is designed to be implantable or is fixed on an orthotic component.

9. The device according to claim 1, wherein the control unit is designed to be implantable.

10. The device according to claim 1, wherein all sensor units are configured to be arranged distally to the knee joint.

11. The device according to claim 1, wherein an inductive energy and information transfer unit is assigned to the control unit.

12. A method for influencing the gait of a patient using the device of claim 1, comprising:
    capturing with the sensor unit at least one of positions of the foot, the lower leg or thigh and at least one of forces, accelerations and momenta acting on the foot, the lower leg or thigh of the patient;
    transmitting the sensor values captured by the sensor unit to the control unit;
    activating at least one foot lifter muscle of the patient via the at least one foot lifter stimulation electrode;
    activating the at least one hip flexor stimulation electrode depending on the activation of the foot lifter muscle.

13. The method according to claim 12, wherein the stimulation electrodes are activated via a common control unit.

14. The method according to claim 12, wherein the stimulation electrodes are activated wirelessly by the control unit.

15. The method according to claim 12, wherein a first of the stimulation electrodes is activated by a first control unit and a second of the stimulation electrodes is activated by a second control unit, and both control units communicate with one another wirelessly.

16. A gait device, comprising;
    at least one foot lifter stimulation electrode to activate a foot lifter muscle;
    at least one sensor unit;
    at least one implantable hip flexor stimulation electrode to activate a hip flexor muscle;
    at least one control unit coupled to the sensor unit and the foot lifter and hip flexor stimulation electrodes and operable to process sensor values from the sensor unit and, depending on the sensor values, activate at least one foot lifter simulation electrode followed by activating the at least one implantable hip flexor stimulation electrode according to a hierarchical structure of the at least one control unit to stimulate a user's muscle to influence a gait of the user.

17. The gait device according to claim 16, wherein the at least one foot lifter stimulation electrode is designed as a surface electrode or as an implant, and the at least one hip flexor stimulation electrode is designed as an implant.

18. The gait device according to claim 16, wherein each stimulation electrode is coupled to a common control unit, or the at least one foot lifter stimulation electrode and the at least one hip flexor stimulation electrode are coupled to separate control units.

* * * * *